US007378636B2

(12) United States Patent
Wada et al.

(10) Patent No.: US 7,378,636 B2
(45) Date of Patent: May 27, 2008

(54) METHOD OF EVALUATING NON-LINEAR OPTICAL CRYSTAL AND DEVICE THEREFOR AND WAVELENGTH CONVERSION METHOD AND DEVICE THEREFOR

(75) Inventors: Satoshi Wada, Wako (JP); Hideo Tashiro, Wako (JP); Masataka Morita, Wako (JP)

(73) Assignee: RIKEN, Wako-Shi, Saitama (JP)

( * ) Notice: Subject to any disclaimer, the term of this patent is extended or adjusted under 35 U.S.C. 154(b) by 373 days.

(21) Appl. No.: 10/504,290

(22) PCT Filed: Feb. 13, 2003

(86) PCT No.: PCT/JP03/01491

§ 371 (c)(1),
(2), (4) Date: Oct. 12, 2004

(87) PCT Pub. No.: WO03/069300

PCT Pub. Date: Aug. 21, 2003

(65) Prior Publication Data

US 2005/0105082 A1    May 19, 2005

(30) Foreign Application Priority Data

Feb. 13, 2002    (JP)    ............................. 2002-035214

(51) Int. Cl.
*G02B 23/04* (2006.01)
*G02F 2/02* (2006.01)
(52) U.S. Cl. ............................. 250/214 VT; 359/326; 359/328

(58) Field of Classification Search ........ 359/237–239, 359/326–328; 372/22, 70, 98; 250/214 VT, 250/251.1, 492.1
See application file for complete search history.

(56) References Cited

U.S. PATENT DOCUMENTS

| 5,032,714 | A | * | 7/1991 | Takahashi et al. | .... 250/214 VT |
| 5,109,462 | A | * | 4/1992 | Watanabe et al. | ........... 359/328 |
| 5,367,531 | A | * | 11/1994 | Eguchi et al. | ................ 372/98 |
| 5,432,807 | A | * | 7/1995 | Okazaki et al. | ................ 372/22 |
| 5,741,595 | A | * | 4/1998 | Wada et al. | ................ 428/426 |
| 6,128,030 | A | * | 10/2000 | Kikuchi et al. | ............. 347/255 |
| 6,249,371 | B1 | * | 6/2001 | Masuda et al. | ............. 359/326 |
| 6,614,584 | B1 | * | 9/2003 | Govorkov et al. | .......... 359/328 |

FOREIGN PATENT DOCUMENTS

| CA | 2303474 A1 | 7/2001 |
| EP | 0420692 A2 | 4/1991 |

(Continued)

*Primary Examiner*—Sang H. Nguyen
(74) *Attorney, Agent, or Firm*—Birch, Stewart, Kolasch & Birch, LLP

(57) ABSTRACT

A method of evaluating a non-linear optical crystal used for non-linear wavelength conversion of laser beam which enables the non-linear optical crystal to be evaluated before the crystal is actually used as a wavelength conversion element in order for the crystal to be constantly used for an extended time with a high conversion efficiency retained and without lowering in output when non-linear optical crystals for various non-linear wavelength conversions such as a CLBO crystal are used to convert laser beams, wherein the non-linear optical crystal is moved to changed a laser beam incident position to detect the output of a laser beam emitted from the non-linear optical crystal for each changing position.

4 Claims, 7 Drawing Sheets

FOREIGN PATENT DOCUMENTS

| | | |
|---|---|---|
| EP | 1116977 A2 | 7/2001 |
| JP | 4-19547 A | 1/1992 |
| JP | 05165072 A * | 6/1993 |
| JP | 05241218 A * | 9/1993 |
| JP | 2000-346802 A | 12/2000 |
| JP | 2001-66654 A | 3/2001 |
| JP | 2001-196669 A | 7/2001 |

* cited by examiner

METHOD OF EVALUATING NON-LINEAR OPTICAL CRYSTAL AND DEVICE THEREFOR AND WAVELENGTH CONVERSION METHOD AND DEVICE THEREFOR

TECHNICAL FIELD

The present invention relates to a method of evaluating a non-linear optical crystal and a device therefor, and a wavelength conversion method and a device therefor. More specifically, the invention relates to a method of evaluating a non-linear optical crystal and a device therefor, which are preferably used in evaluating a non-linear optical crystal used for non-linear wavelength conversion of laser beam, and a wavelength conversion method and a device therefor.

BACKGROUND ART

Currently, laser beam having wavelength of an ultraviolet region has been used for microfabrication of metals, reading devices of optical discs, and the like.

Conventionally, such laser beam having wavelength of the ultraviolet region has been generated by using gas laser such as excimer laser.

However, gas laser has problems of low operation efficiency and short lifetime, and also has a problem that $F_2$ gas, for example, which is used as operating gas has toxicity. Further, a problem of high operating voltage has been also pointed out.

For these reasons, technology has been proposed to generate laser beam having wavelength in the ultraviolet region by solid-state laser using a non-linear optical crystal instead of gas laser.

As such technology, a technology is known where non-linear wavelength conversion is performed to laser beam having the wavelength of 532 nm, which is the second harmonic of the Nd:YAG laser, into laser beam in an ultraviolet region with the wavelength of 266 nm by using a cesium-lithium-borate crystal (CLBO crystal).

Meanwhile, the inventor of the present invention discovered that the CLBO crystal, because it is uneven and the crystal has irregularity, had a problem of reduction of output in a very short time by the generation of damage on the crystal caused by ultraviolet ray, which is created by the non-linear wavelength conversion, depending on a region to which laser beam is irradiated for non-linear wavelength conversion. Further, the inventor also discovered a problem that it was impossible to obtain a same output constantly because of the unevenness of crystal even if the region to which the laser beam having the wavelength of 532 nm was changed by simply moving the crystal when the output reduced.

The present invention has been made in view of the above-described problems, and its object is to provide a method of evaluating a non-linear optical crystal and a device therefor, and a wavelength conversion method and a device therefor, which are capable of evaluating the non-linear optical crystal in advance before the non-linear optical crystal is actually used as a wavelength conversion element in order to maintain high conversion efficiency and use the non-linear optical crystal stably for a long period of time without reducing output in the case where laser beam wavelength is converted by using any of various kinds of non-linear optical crystal for non-linear wavelength conversion such as a CLBO crystal.

DISCLOSURE OF INVENTION

To achieve the above-described objects, the present invention is a method of evaluating non-linear optical crystal used for a non-linear wavelength conversion of laser beam, in which the non-linear optical crystal is moved to change a laser beam incident position, and the output of laser beam emitted from the non-linear optical crystal is detected for each of the changing positions.

Further, the present invention is a non-linear optical crystal evaluation device used for non-linear wavelength conversion of laser beam, in which the device has moving means for moving the non-linear optical crystal to change a laser beam incident position, and detection means for detecting the output of laser beam emitted from the non-linear optical crystal for each laser beam incident position that changes with the movement of the non-linear optical crystal moved by the moving means.

Furthermore, the present invention is a non-linear optical crystal evaluation device used for non-linear wavelength conversion of laser beam, in which the device has the moving means for moving the non-linear optical crystal to change the laser beam incident position, the detection means for detecting the output of laser beam emitted from the non-linear optical crystal for each of the laser beam incident positions that change when the non-linear optical crystal is moved by the moving means, and storage means for storing the detection result of the detection means.

Still further, the present invention is one where the storage means is a freely detachable storage medium.

Further, the present invention is a wavelength conversion method of laser beam by non-linear wavelength conversion using a non-linear optical crystal, in which the non-linear optical crystal is moved to change the laser beam incident position, the output of laser beam emitted from the non-linear optical crystal is detected for each changing position, and positions whose output shows a predetermined value or higher are selected from the changing positions based on the detection result and laser beam is made incident to the positions to perform non-linear wavelength conversion.

Furthermore, the present invention is a wavelength conversion device of laser beam by non-linear wavelength conversion using a non-linear optical crystal, in which the device has moving means for moving the non-linear optical crystal to change the laser beam incident position, detection means for detecting the output of laser beam emitted from the non-linear optical crystal for each laser beam incident position that changes with the movement of the non-linear optical crystal moved by the moving means, and control means for selecting positions whose output shows a predetermined value or higher from the laser beam incident positions based on the detection result by the detection means and making laser beam incident to the positions.

Still further, the present invention is a wavelength conversion device of laser beam by non-linear wavelength conversion using non-linear optical crystal, in which the device has moving means for moving the non-linear optical crystal to change the laser beam incident position, detection means for detecting the output of laser beam emitted from the non-linear optical crystal for the laser beam incident position that changes with the movement of the non-linear optical crystal moved by the moving means, storage means for storing the detection result of the detection means, and control means for selecting positions whose output shows a predetermined value or higher from the laser beam incident positions based on the detection result by the detection means and making laser beam incident to the positions.

Further, the present invention is one where the storage means is a freely detachable storage medium.

Therefore, by using the present invention described above, it is possible to avoid the output reduction of a CLBO crystal due to the damage by ultraviolet light by automatically moving the CLBO crystal in a wavelength conversion device utilizing the CLBO crystal that has drawn attention as the non-linear optical crystal for generating ultraviolet light in recent years, for example.

At this point, unevenness at each area of the CLBO crystal is detected, areas of the CLBO crystal which are usable at a constant level are clarified, and the CLBO crystal is moved such that laser beam is sequentially irradiated only on the areas usable at a constant level.

This is the invention that has been created for the first time on the basis of understanding the property of CLBO crystal, which has not been known, that unevenness exists in the CLBO crystal or unevenness easily occurs even after the CLBO crystal is fabricated.

According to the present invention, it is possible to provide a high-power ultraviolet laser for processing efficiently and with long lifetime.

Particularly, when the storage means is constituted as a freely detachable storage medium and the detection result from the detection means is stored in the freely detachable storage medium, the detection result stored in the storage medium is made compatible between the non-linear optical crystal evaluation device according to the present invention and the wavelength conversion device according to the present invention, and sharing of the detection result stored in the storage medium becomes extremely easy between the non-linear optical crystal evaluation device according to the present invention and the wavelength conversion device according to the present invention. When the detection result stored in the storage medium is shared between the non-linear optical crystal evaluation device according to the present invention and the wavelength conversion device according to the present invention, the detection result obtained by the non-linear optical crystal evaluation device according to the present invention can be reflected on the wavelength conversion device according to the present invention.

EXPLANATION OF REFERENCE NUMERALS

Figure 1:
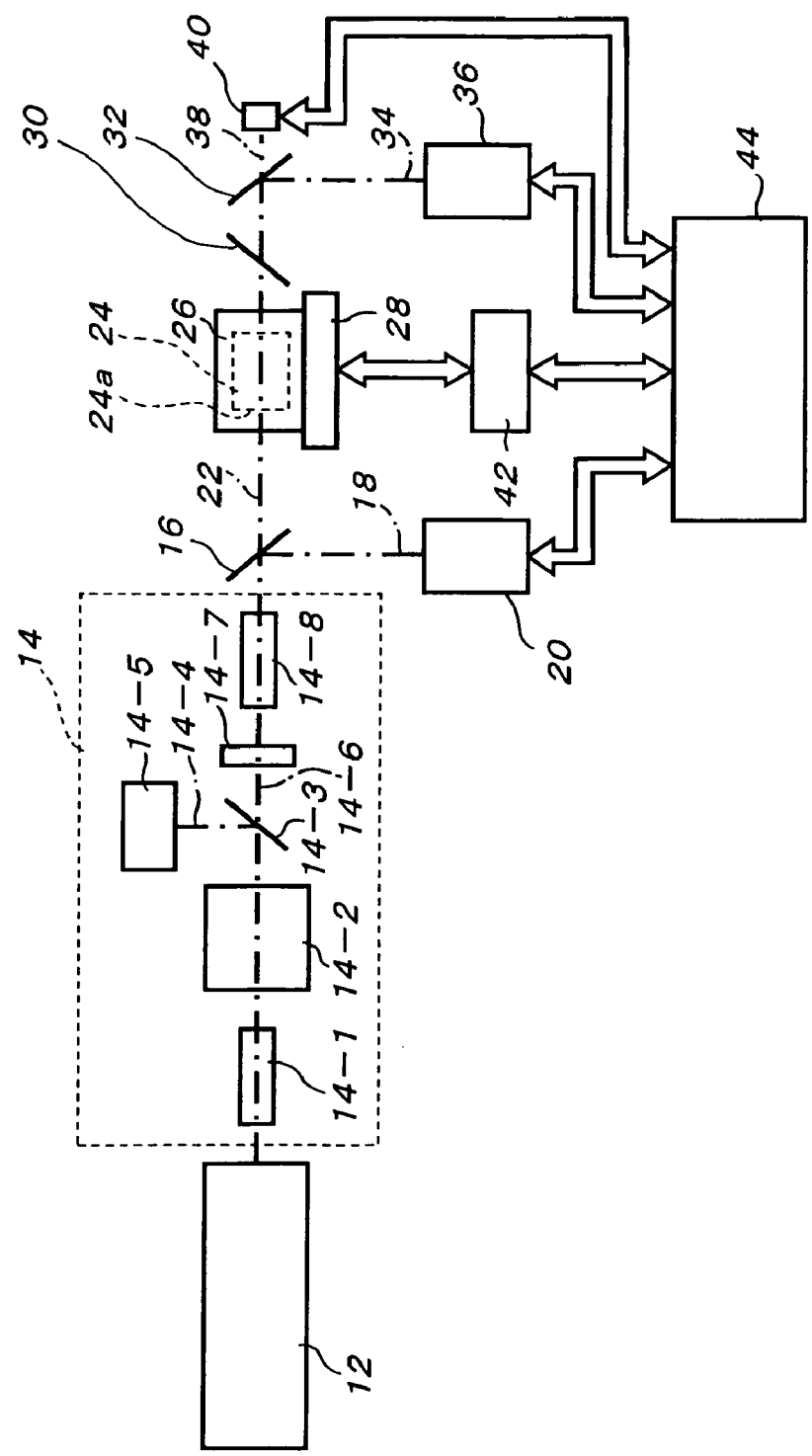
FIG. 1 is a schematic constitutional exemplary drawing showing an example of an embodiment of the evaluation device of a non-linear optical crystal according to the present invention.

12 . . . Pumping laser
14 . . . Output control unit
16 . . . First separating mirror
18 . . . Optical path
20 . . . First mode master
22 . . . Optical path of laser beam
24 . . . CLBO crystal
26 . . . Holder
28 . . . Moving stage
30 . . . Damper
32 . . . Second separating mirror
34 . . . Optical path
36 . . . Second mode master
38 . . . Optical path
40 . . . Output detector
42 . . . Driving unit
44 . . . Computer
46 . . . Fourth separating mirror
48 . . . Optical path
50 . . . Optical path

BEST MODE FOR CARRYING OUT THE INVENTION

In the following, description will be made in detail for an example of embodiments of the evaluation method of a non-linear optical crystal and device therefor and the wavelength conversion method and the device therefor according to the present invention based on the accompanying drawings.

FIG. 1 shows the schematic constitutional exemplary drawing showing an example of the embodiment of the evaluation device of a non-linear optical crystal according to the present invention. It is to be noted that the non-linear optical crystal evaluation device shown in FIG. 1 shows an example where the device is used for evaluating a CLBO crystal as the non-linear optical crystal that performs non-linear wavelength conversion to laser beam output from Nd:YAG laser having the wavelength of 532 nm, which is the second harmonic, into laser beam in an ultraviolet region having the wavelength of 266 nm.

The non-linear optical crystal evaluation device is constituted by having a pumping laser 12 made up of the Nd:YAG laser that emits laser beam having the wavelength of 532 nm as the second harmonic, an output control unit 14 that controls the output of the laser beam having the wavelength of 532 nm emitted from the pumping laser 12, a first separating mirror 16 that splits the laser beam emitted from the output control unit 14 into two optical paths, a first mode master that detects the beam profile of the laser beam on an optical path 18 that is one of the optical paths split into two by the first separating mirror 16, a holder 26 in which a CLBO crystal 24, to which an optical path 22 that is another one of the optical paths split into two by the first separating mirror 16 is made incident, is arranged in a vacuum sealed state (it is to be noted that the vacuum degree of the holder 26 is set to $10^0$ to $10^2$ Torr, for example), a moving stage 28 that mounts the holder 26 and moves the holder 26 on a plane orthogonal to the optical path 22 (hereinafter, referred to as a "holder moving plane"), a damper 30 that cancels the component of the wavelength of 532 nm from the laser beam emitted from the holder 26 after non-linear wavelength conversion is performed by the CLBO crystal 24, a second separating mirror 32 that splits the laser beam passed through the damper 30 into two optical paths, a second mode master 36 that detects the beam profile of the laser beam on an optical path 34 that is another one of the optical paths split into two by the second separating mirror 32, an output detector 40 that detects the output of laser beam on an optical path 38, which is another one of the optical paths split into two by the second separating mirror 32, a driving unit 42 made up of a motor or the like that drives the moving stage 28 so as to move the holder 26 on the holder moving plane, and a computer 44 that controls the first mode master 20, the second mode master 36, the output detector 40 and the driving unit 42.

It is to be noted that the output control unit 14 is constituted by having a first telescope 14-1 that condenses the laser beam having the wavelength of 532 nm, which is emitted from the pumping laser 12, an output variable unit 14-2 that varies the output of the laser beam emitted from the first telescope 14-1, a third separating mirror 14-3 that splits the laser beam emitted from the output variable unit 14-2 into two optical paths, an output detector 14-5 that detects the output of laser beam on an optical path 14-4, which is one of the optical paths split into two by the third separating mirror 14-3, a polarization rotator 14-7 that controls the polarization of laser beam on an optical path 14-6, which is another one of the optical paths split into two by the third separating mirror 14-3, and a second telescope 14-8 that condenses the laser beam passed through the polarization rotator 14-7.

The driving unit 42 drives the moving stage 28 according to control signals from the computer 44, and moves the holder 26 mounted on the moving stage 28 on the holder moving plane. The movement of the holder 26 on the holder moving plane makes it possible to change the incident position on the CLBO crystal 24 when the laser beam on the optical path 22 is made incident to the CLBO crystal 24.

Herein, the storage means built in the computer 44 is provided with a storage region that stores the track of movement of an irradiating position of the laser beam, which travels on the optical path 22, on the CLBO crystal 24 arranged in the holder 26 that is moved with the driving of the moving stage 28 by the driving unit 42.

Further, the detection results of the beam profile of laser beam, which were severally detected by the first mode master 20 and the second mode master 36, and the detection result of the output of laser beam detected by the output detector 40 are input to the computer 44. A storage region, which stores the detection results corresponding to the track of movement of the irradiating position of the laser beam on the optical path 22 on the CLBO crystal 24, is set in the storage means built in the computer 44.

Figure 2:
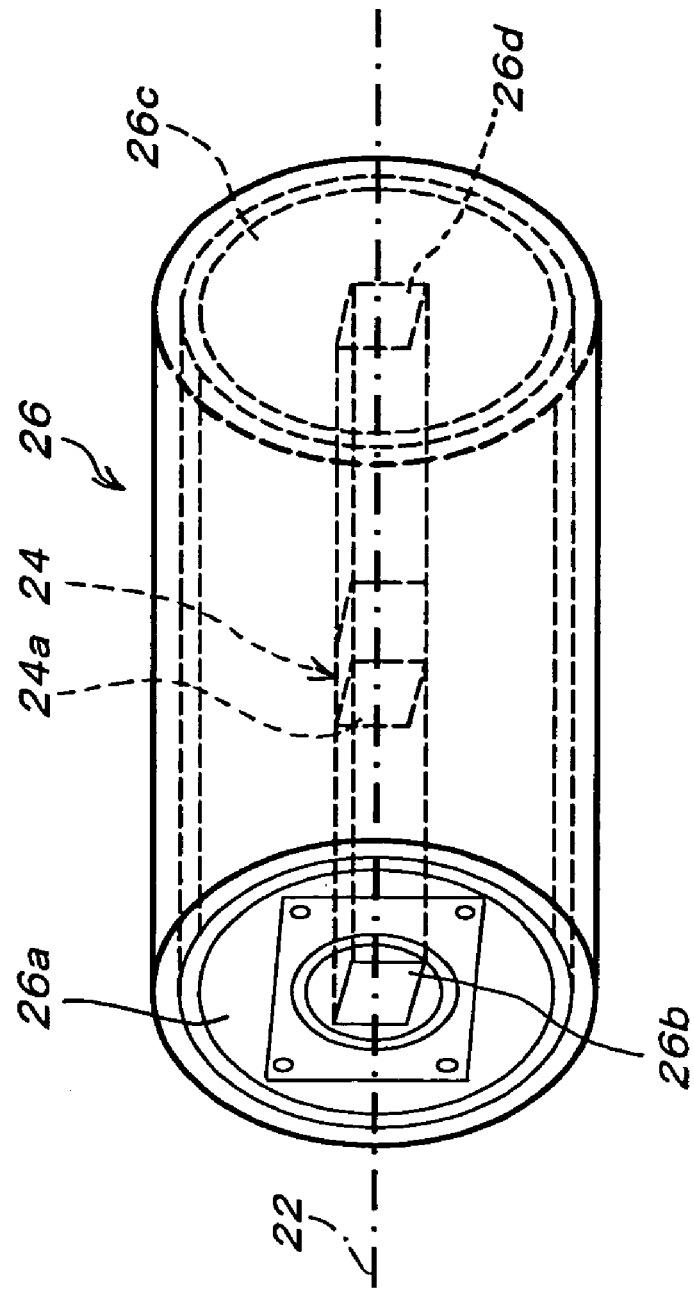
FIG. 2 is a schematic constitutional perspective view of a holder.

FIG. 2 shows the schematic constitutional perspective view of the holder 26. The holder 26 is a cylindrical hermetically sealed container, and the CLBO crystal 24 of an oblong cubic shape is arranged in an approximately central area in the container. It is to be noted that the CLBO crystal 24 is arranged such that a plane 24a to which the laser beam traveling the optical path 22 is made incident (hereinafter, referred to as an "incident plane") becomes orthogonal to the laser beam traveling the optical path 22.

A window 26b formed by a transparent material is disposed for the laser beam on the optical path 22 in an approximately central area of an incident side end surface 26a of the holder 26, to which the laser beam on the optical path 22 is made incident, and a window 26d formed by a transparent material is disposed for the laser beam emitted from the CLBO crystal 24 in an approximately central area of an emitting side end surface 26c of the holder 26, to which the laser beam emitted from the CLBO crystal 24 is made incident.

Figure 3:
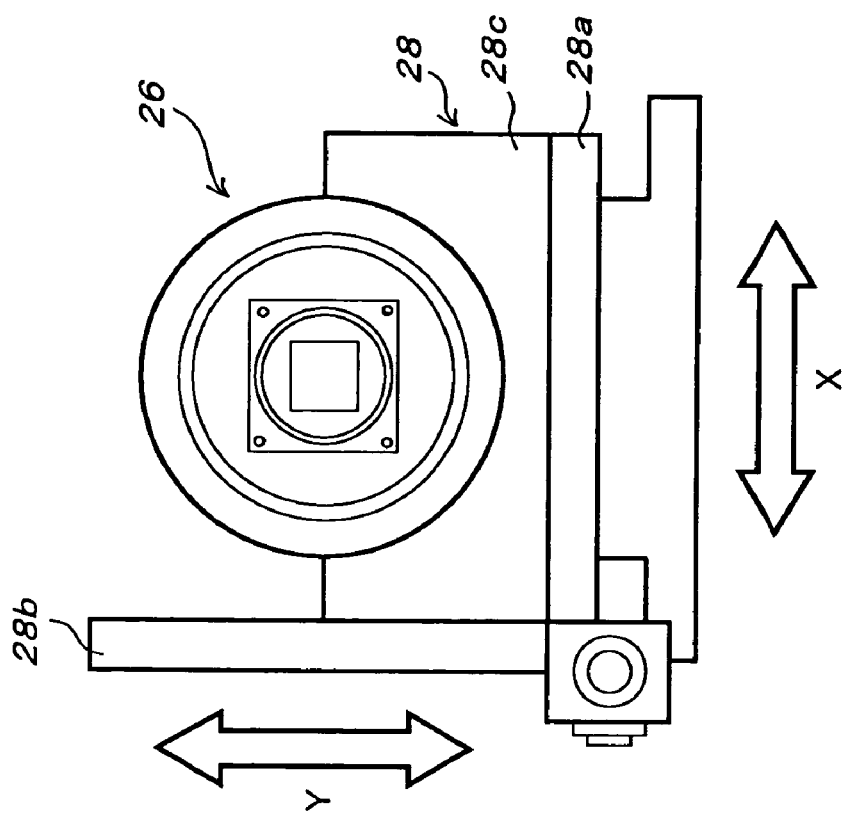
FIG. 3 is a schematic constitutional exemplary drawing of a moving stage on which the holder is arranged.

FIG. 3 shows the schematic constitutional exemplary drawing of the moving stage 28 on which the holder 26 is arranged. The moving stage 28 is constituted by having a first axis (hereinafter, referred to as an "X-axis") 28a and a second axis (hereinafter, referred to as a "Y-axis") 28b, which are arranged to be severally orthogonal to the laser beam on the optical path 22 and orthogonal to each other so as to constitute an X-Y plane, and a holder support 26c that is arranged freely slidably along the X-axis 28a and the Y-axis 28b individually and supports the holder 26.

When the computer 44 controls the driving unit 42, the driving unit 42 moves the holder support 26c supporting the holder 26 along the first axis 28a and the second axis 28b, and as a result, the CLBO crystal 24 arranged inside the holder 26 moves on the holder moving plane and changes the incident position on the CLBO crystal 24 when the laser beam on the optical path 22 is made incident to the CLBO crystal 24.

With the above-described constitution, the controlling method of the non-linear optical crystal evaluation device will be described in detail.

To evaluate the CLBO crystal by using the non-linear optical crystal evaluation device, the CLBO crystal 24 to be evaluated is arranged inside the holder 26, and the holder 26 is mounted on the holder support 26c of the moving stage 28 to allow the support to support it.

Next, the output variable unit 14-2 of the output control unit 14 variably controls the output of laser beam emitted from the pumping laser 12, and the output of laser beam that is made incident to the CLBO crystal 24 is set to a predetermined value to perform optimization while the output detector 14-5 monitors the variably controlled output.

Then, the polarization rotator 14-7 is rotated to optimize the polarization of the laser beam that is made incident to the CLBO crystal 24.

Subsequently, the computer 44 controls the driving unit 42 to move the holder 24 mounted on the moving stage 28 along the holder moving plane, the incident position of the laser beam on the optical path 22 on the CLBO crystal 24 is changed over the entire surface of the incident plane 24a, and the detection results of the first mode master 20, the second mode master 36 and the output detector 40 are recorded every time when the incident position is changed.

Resolving power when the incident position of the laser beam on the optical path 22 on the CLBO crystal 24 is changed over the entire surface of the incident plane 24a depends on the throughput of the computer 44, the structure and the detecting capability of the driving unit 42, the moving stage 28, the first mode master 20, the second mode master 36 and the output detector 40. For example, when Gaussian beam having the diameter of 100 μm is used as pumping beam, it is preferable that an interval of the moving distance of the incident position be a smallest possible distance of 300 μm or more. More specifically, it is preferable that the lowest limit have a smallest moving distance about three times the laser beam to be used in order to prevent spatial overlap.

As described above, the beam profile of the laser beam before it is made incident to the CLBO crystal 24, the beam profile of the laser beam emitted from the CLBO crystal 24, and the output of the laser beam emitted from the CLBO crystal 24 corresponding to the incident position of laser beam on the optical path 22 are stored in a predetermined storage region of the storage means of the computer 44 with regard to the entire region of the incident plane 24a of the CLBO crystal 24.

Figure 4:
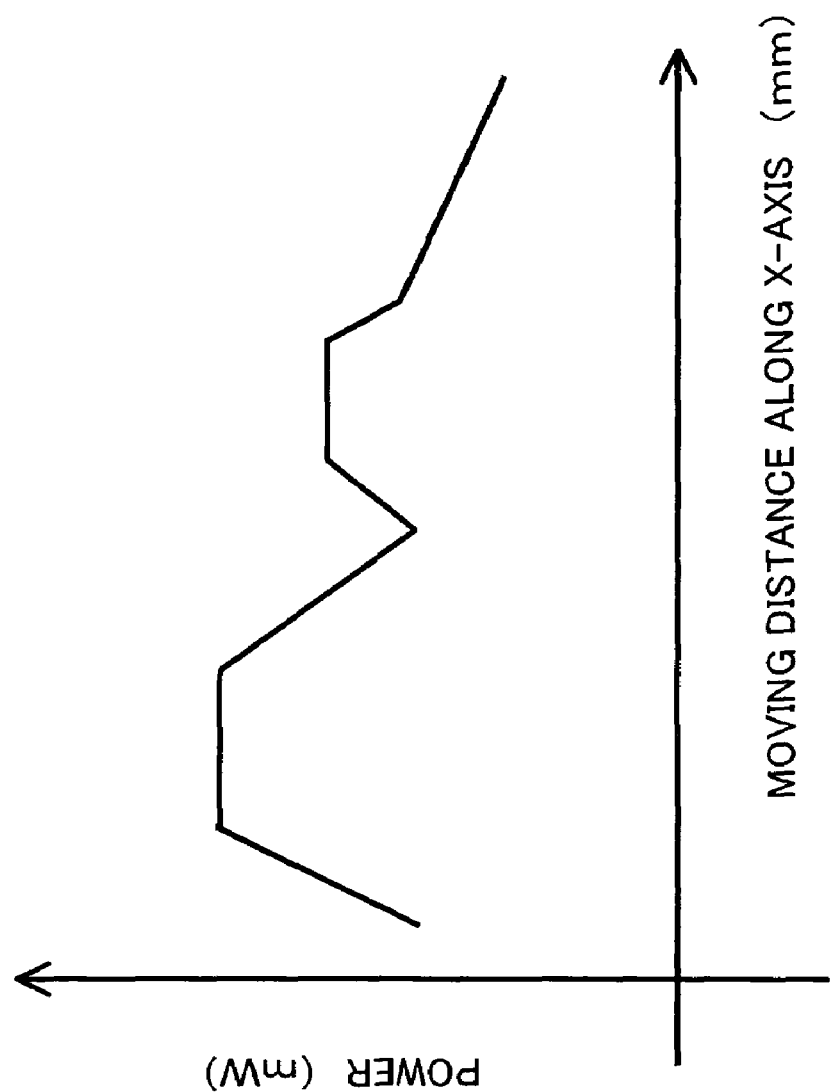
FIG. 4 is a graph showing the changes of output of laser beam emitted from a CLBO crystal with the changes of laser beam incident position along an x-axis on an incident plane of the CLBO crystal, and it shows the relation between the irradiation position and the output of laser beam.

FIG. 4 shows an example of the graph that is formed based on the above-described stored content stored in the predetermined storage region of the storage means of the computer 44, and the graph shows the changes of the output of laser beam emitted from the CLBO crystal 24 with the changes of the incident position of the optical path 22 of laser beam along the X-axis 28a on the incident plane 24a of the CLBO crystal 24 (that is, the movement of the laser beam incident position in the one dimensional direction).

Figure 6:
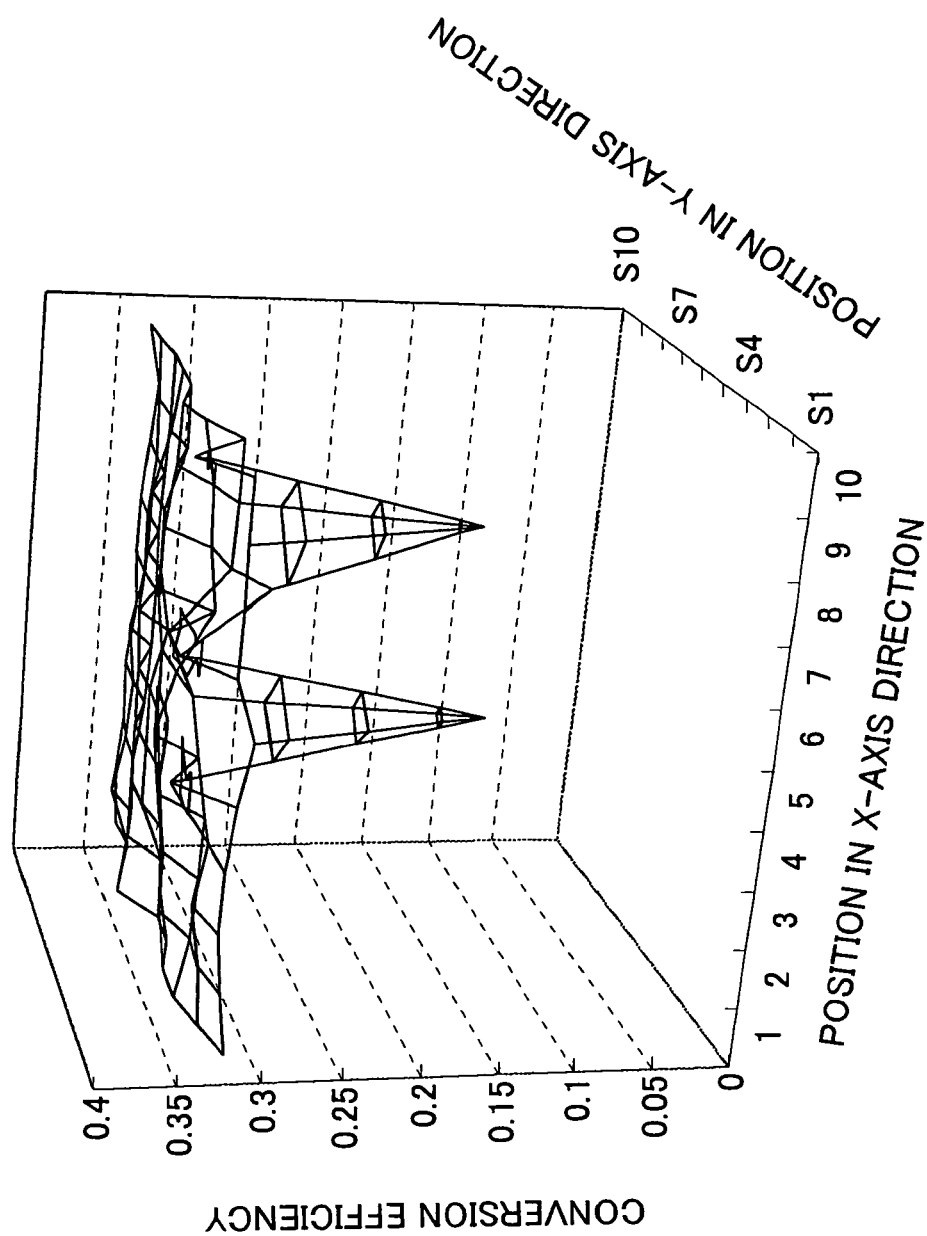
FIG. 6 is a graph showing the changes of conversion efficiency with the changes of laser beam incident positions on the entire surface of the incident plane of the CLBO crystal (the efficiency corresponds to the output of laser beam emitted from the CLBO crystal which is normalized by the output of incident laser to the CLBO crystal).

FIG. 6 shows another example of the graph that is formed based on the above-described stored content stored in the predetermined storage region of the storage means of the computer 44, and the graph shows the changes of conversion efficiency with the changes of the incident positions of the optical path 22 of laser beam on the entire surface of the incident plane 24a of the CLBO crystal 24 along the X-axis 28a and the Y-axis 28b (that is, the movement of the laser beam incident position in the two dimensional direction). It is to be noted that the interval of the moving distance of the laser beam incident position is 100 mµ, and a measurement range is "1 mm (horizontal: X-axis 28a direction)×1 mm (vertical: Y-axis 28b direction)".

As shown on the graphs of FIGS. 4 and 6, the output, that is, the conversion efficiency of the CLBO crystal 24 changes depending on the irradiation position of laser beam.

Therefore, using the detection result by the non-linear optical crystal evaluation device makes it possible to easily determine on which position of the incident plane 24a of the CLBO crystal 24, whose output (that is, the conversion efficiency) changes depending on the laser beam irradiation position, the laser beam should be irradiated in order to obtain high conversion efficiency, and thus the CLBO crystal 24 can be evaluated.

It is to be noted that such determination and evaluation can be performed by using a computer using known technology.

Then, in the case of utilizing the laser beam emitted from the CLBO crystal 24 in processing a subject to be processed, when the CLBO crystal 24 evaluated as described above is used, the laser beam is made incident only at positions where high conversion efficiency is obtained based on the detection result while the laser beam incident position on the incident plane 24a of the CLBO crystal 24 is sequentially moved, and thus the laser beam can be utilized efficiently.

For example, it is possible to avoid the output reduction of the CLBO crystal 24 due to the damage by ultraviolet light by automatically moving the CLBO crystal 24.

Figure 7:
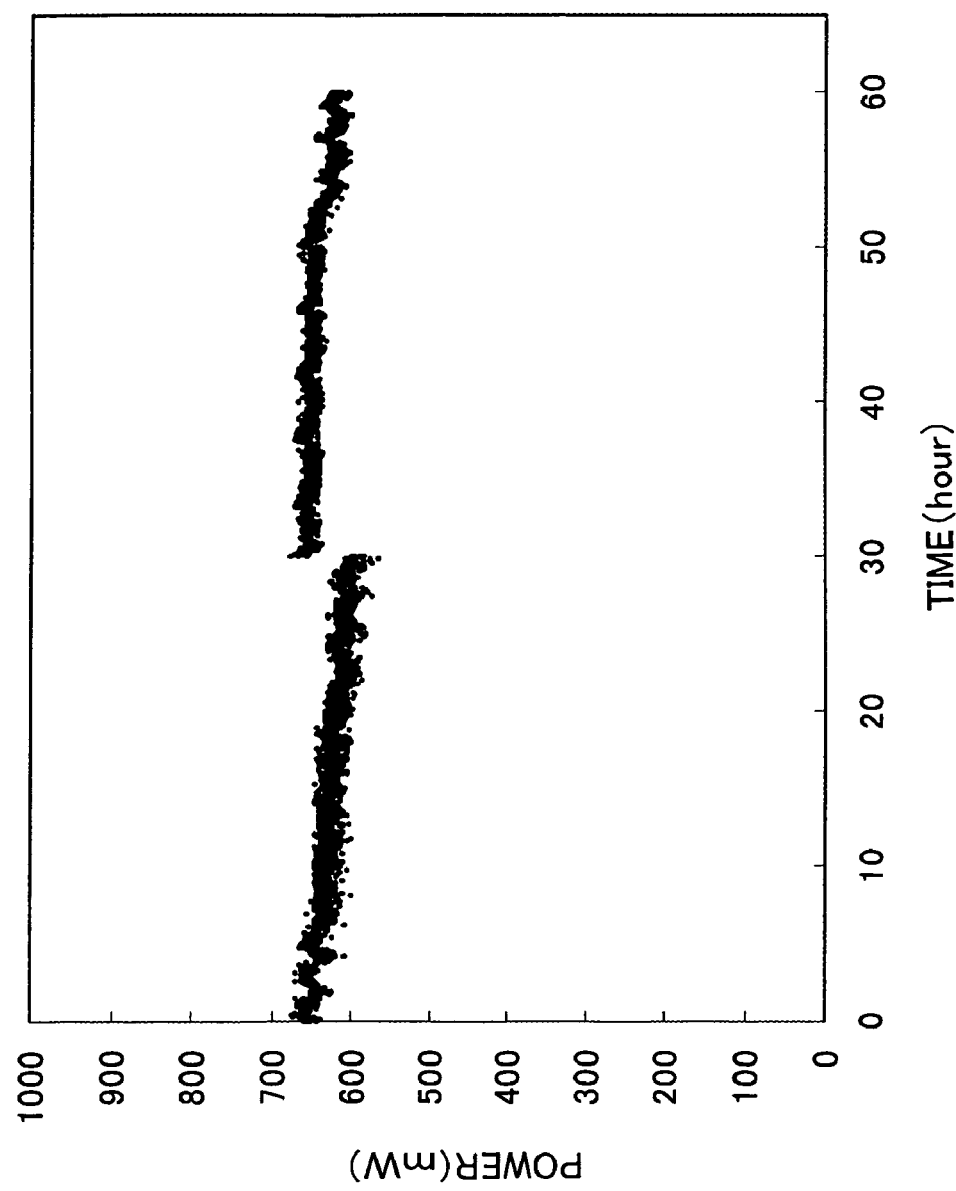
FIG. 7 is a graph in which axis of abscissas takes incidence time where laser beam was made incident to the incident plane of the CLBO crystal and axis of ordinate takes the output of laser beam emitted from the CLBO crystal, and shows a result obtained when a laser beam incident position was moved after laser beam was made incident to a same incident position on the incident plane of the CLBO crystal for 30 hours and laser beam was made incident to the moved incident position for another 30 hours.

FIG. 7 shows the graph in which axis of abscissas takes incidence time where laser beam was made incident to the incident plane of the CLBO crystal and axis of ordinate takes the output of laser beam emitted from the CLBO crystal, and the graph shows the result obtained when the laser beam incident position was moved after the laser beam was made incident to a same incident position on the incident plane 24a of the CLBO crystal 24 for 30 hours and the laser beam was made incident to the moved incident position for another 30 hours.

As is also clear from FIG. 7, although the intensity of the laser beam output from the CLBO crystal 24 reduces with time due to the damage by ultraviolet light, the intensity of the laser beam output from the CLBO crystal 24 can be returned to an initial value when the laser beam incident position is moved.

Figure 5:
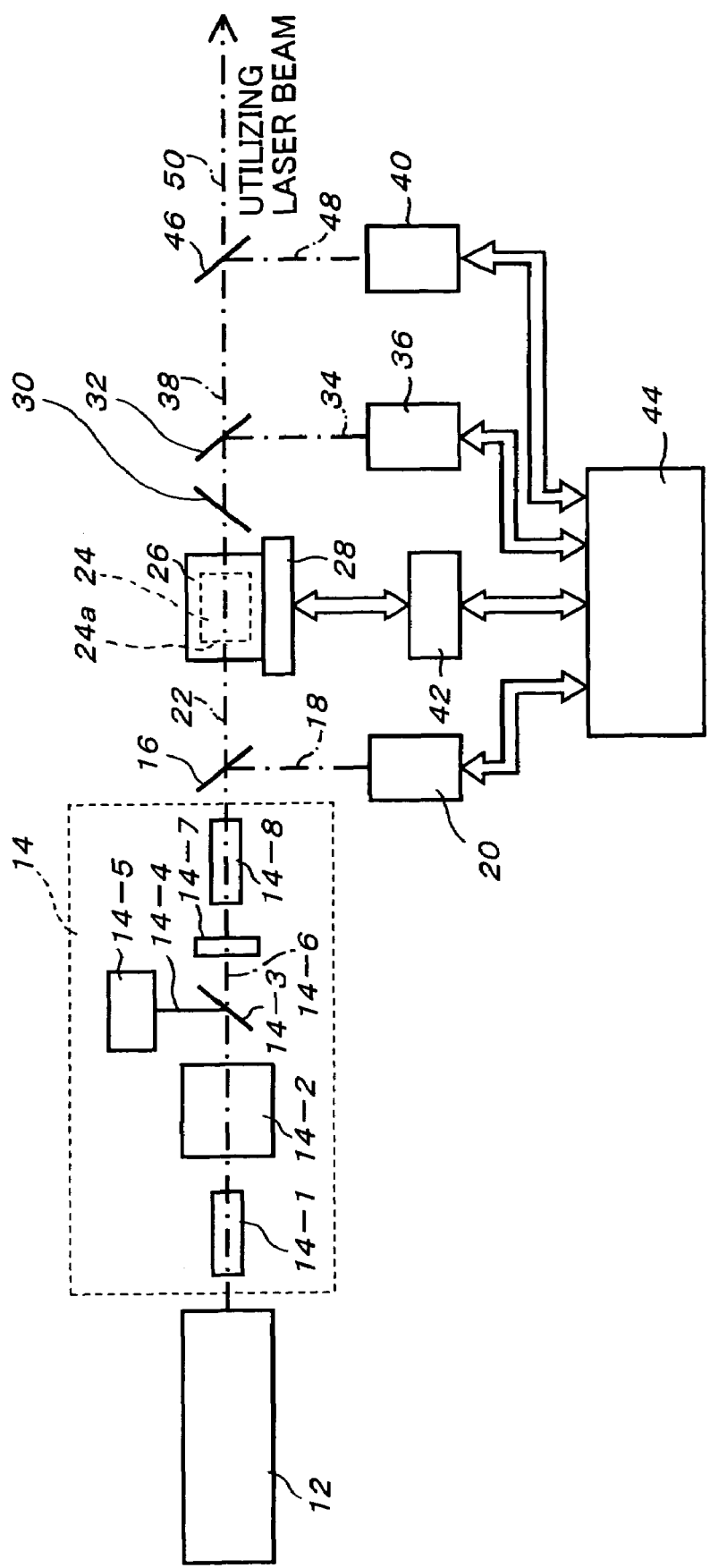
FIG. 5 is a schematic constitutional exemplary drawing of a frequency conversion device using the evaluation method of a non-linear optical crystal according to the present invention.

FIG. 5 shows the schematic constitutional exemplary drawing of the frequency conversion device using the above-described evaluation method of a non-linear optical crystal.

Meanwhile, in the frequency conversion device shown in FIG. 5, description of the detail constitution and operation will be omitted for constitution same as the constitution shown in the evaluation method of non-linear optical crystal shown in FIG. 1 by showing the same reference numerals as the reference numerals used in the description of FIG. 1.

In the frequency conversion device, the optical path 38 that is another one of the optical paths split into two by the second separating mirror 32 is further split into two optical paths by a fourth separating mirror 46.

Then, the output detector 44 detects the laser beam on an optical path 48 that is one of the optical paths split into two by the fourth separating mirror 46.

On the other hand, the laser beam on an optical path 50 that is another one of the optical paths split into two by the fourth separating mirror 46 should be utilized for processing the subject to be processed.

On such occasion, similar to the above-described non-linear optical crystal evaluation device, after evaluating the non-linear optical crystal in advance, laser beam irradiation positions on the incident plane 24a of the CLBO crystal 24 should be determined according to the evaluation result. Specifically, the detection result on the incident positions of laser beam on the incident plane 24a, which is stored in the computer 44, is read out, optimum positions from which a constant output or more is obtained are selected by the automatic control of the computer 44 to sequentially move the CLBO crystal 24, and the laser beam should be made incident on the optimum positions.

It is to be noted that the above-described embodiments may be modified as shown in (1) to (4) below.

(1) In the above-described embodiments, the storage means built in the computer 44 was made to store the track of movement of the irradiating position of the laser beam, which travels on the optical path 22, on the CLBO crystal 24 arranged in the holder 26 that is moved with the driving of the moving stage 28 by the driving unit 42, or to store the detection results of the beam profile of laser beam, which were severally detected by the first mode master 20 and the second mode master 36, and the detection result of the output of laser beam detected by the output detector 40 corresponding to the track of movement of the irradiating position of the laser beam on the optical path 22 on the CLBO crystal 24. However, it goes without saying that the invention is not limited to this.

For example, various kinds of freely detachable storage medium such as a flexible disc and a magnetic optical disc may be used to store the above-described various kinds of information instead of the storage means built in the computer 44.

When various information including the detection results of the beam profile of laser beam, which were severally detected by the first mode master 20 and the second mode master 36, and the detection result of the output of laser beam detected by the output detector 40 is stored in the freely detachable medium, the various information stored in the storage medium is made compatible between the non-linear optical crystal evaluation device according to the present invention and the wavelength conversion device according to the present invention, and sharing of the various information stored in the storage medium becomes extremely easy between the non-linear optical crystal evaluation device according to the present invention and the wavelength conversion device according to the present invention. When the various information stored in the storage medium is shared between the non-linear optical crystal evaluation device according to the present invention and the wavelength conversion device according to the present invention, the detection result obtained by the non-linear optical crystal evaluation device according to the present invention can be reflected on the wavelength conversion device according to the present invention.

(2) In the above-described embodiments, description has been made for the case where the CLBO crystal was used as a crystal to be evaluated, but it goes without saying that the crystal to be evaluated is not limited to the CLBO crystal. The present invention is capable of evaluating various kinds of crystal such as an LBO crystal, a BBO crystal and a KTP crystal.

(3) In the above-described embodiments, description has been made for the frequency conversion device where the laser beam emitted from the device was made to process the subject to be processed, but it goes without saying that the use of the laser beam emitted from the frequency conversion device is not limited to the processing of the subject to be processed. For example, the laser beam can be used for a reading device of an optical disc, a three dimensional molding system, or medical practice.

(4) The above-described embodiments and the modifications shown in (1) to (3) above may be properly combined.

INDUSTRIAL APPLICABILITY

Since the present invention is constituted as described above, it exerts superior effect that the a non-linear optical crystal can be evaluated in advance before the non-linear optical crystal is actually used as a frequency conversion element.

What is claimed is:

1. A wavelength conversion method of laser beam by non-linear wavelength conversion using a non-linear optical crystal, comprising the step of:

the non-linear optical crystal is moved along an X-axis and a Y-axis individually, said X-axis and said Y-axis are arranged to be severally orthogonal to an incident laser beam to said non-linear optical crystal and orthogonal to each other so as to constitute an X-Y plane, in order to change an incident position of said incident laser beam in said non-linear optical crystal, output of laser beam emitted from said non-linear optical crystal is detected for each incident position of said incident laser beam that is changed by movement of said non-linear optical crystal; and positions where said output of laser beam emitted from said non-linear optical crystal whose output shows a predetermined value or higher are selected from said incident positions of said incident laser beam in said non-linear optical crystal based on detection result and laser beam is made incident to the positions to perform non-linear wavelength conversion.

2. A wavelength conversion device of laser beam by non-linear wavelength conversion using a non-linear optical crystal, comprising:

moving means for moving the non-linear optical crystal along an X-axis and a Y-axis individually, said X-axis and said Y-axis are arranged to be severally orthogonal to an incident laser beam to said non-linear optical crystal and orthogonal to each other so as to constitute an X-Y plane, in order to change an incident position of said incident laser beam in said non-linear optical crystal;

detection means for detecting output of laser beam emitted from said non-linear optical crystal for each incident position of said incident laser beam that is changed by movement of said non-linear optical crystal moved by said moving means; and control means for selecting positions where said output of laser beam emitted from said non-linear optical crystal shows a predetermined value or higher from said incident positions of said incident laser beam in said non-linear optical crystal based on detection result by said detection means and making said incident laser beam to be incident to said positions.

3. A wavelength conversion device of laser beam by non-linear wavelength conversion using a non-linear optical crystal comprising:

moving means for moving the non-linear optical crystal along an X-axis and a Y-axis individually, said X-axis and said Y-axis are arranged to be severally orthogonal to an incident laser beam to said non-linear optical crystal and orthogonal to each other so as to constitute an X-Y plane, in order to change an incident position of said incident laser beam in said non-linear optical crystal;

detection means for detecting output of laser beam emitted from said non-linear optical crystal for each incident position of said incident laser beam that is changed by movement of said non-linear optical crystal moved by said moving means;

storage means for storing the detection result of said detection means; and control means for selecting positions where said output of laser beam emitted from said non-linear optical crystal shows a predetermined value or higher from said incident positions of said incident laser beam in said non-linear optical crystal based on detection result stored in said storage means and making said incident laser beam to be incident to the positions.

4. The wavelength conversion device according to claim 3, wherein said storage means is a freely detachable storage medium.

* * * * *